United States Patent [19]

Scholz

[11] Patent Number: 4,619,900

[45] Date of Patent: Oct. 28, 1986

[54] SOLVENT FOR THE DETERMINATION OF WATER BY THE KARL FISCHER METHOD

[75] Inventor: Eugen Scholz, Garbsen, Fed. Rep. of Germany

[73] Assignee: Hoechst Aktiengesellschaft, Frankfurt, Fed. Rep. of Germany

[21] Appl. No.: 637,912

[22] Filed: Aug. 6, 1984

[30] Foreign Application Priority Data

Aug. 11, 1983 [DE] Fed. Rep. of Germany ....... 3329020

[51] Int. Cl.⁴ .............................................. G01N 33/18
[52] U.S. Cl. ..................................... 436/42; 204/1 T
[58] Field of Search .................... 436/39–42; 204/1 T; 252/364

[56] References Cited

U.S. PATENT DOCUMENTS

| | | | |
|---|---|---|---|
| 4,056,403 | 11/1977 | Cramer et al. | 252/364 X |
| 4,351,744 | 9/1982 | Muroi et al. | 252/400 |
| 4,354,853 | 10/1982 | Dahms | 204/1 T |
| 4,368,105 | 1/1983 | Muroi et al. | 436/42 |

FOREIGN PATENT DOCUMENTS 2193490  2/1974  France .

OTHER PUBLICATIONS

Karl Fischer, Angew, Chemie 48, pp. 394–396, (1935).
Chemical Analysis, vol. 5, Aquametry, Part III, pp. 100–101 (1980).
Peters et al., Anal. Chem. 27, pp. 450–453 (1955).
Kellum et al., Analytical Chemistry, vol. 42(12), pp. 1428–1429, Oct., 1970.
Petrov et al., Journal of Analytical Chemistry of the USSR, vol. 35(11), pp. 1426–1429, Nov., 1980.

*Primary Examiner*—Arnold Turk
*Attorney, Agent, or Firm*—Curtis, Morris & Safford

[57] ABSTRACT

The determination of water by the Karl Fischer method is carried out using a reagent containing sulfur dioxide, iodine and a base. The determination is carried out in a liquid medium in which the sample under investigation has been dissolved. The solvents used are, above all, methanol and 2-methoxyethanol. The presence of a further solvent which enables the reaction to take place without interference is advantageous. Solvents suitable for this purpose are lower alkanols which are substituted by halogen atoms and/or phenyl radicals. These alkanols are also employed as the solvent in Karl Fischer reagents.

4 Claims, No Drawings

SOLVENT FOR THE DETERMINATION OF WATER BY THE KARL FISCHER METHOD

The invention relates to a solvent and a reagent for the determination of water and to a process for the determination of water in an organic solvent by the Karl Fischer method.

As is known, a reagent developed by Karl Fischer is suitable for the titration of water. The reagent is usually composed of a solution of iodine, sulfur dioxide and pyridine in methanol (cf. Angew. Chemie 48 (1935), 394). In carrying out the determination of water, the sample to be examined is preferably dissolved in methanol and is then titrated with the abovementioned solution. Since this one-component reagent is not stable on storage, in practice a two-component reagent is also used, which comprises firstly a solution of sulfur dioxide and pyridine in methanol (solution A) and secondly a methanolic solution of iodine (solution B). The sample to be examined is dissolved in solution A and is titrated with solution B. An analagous one-component reagent containing the iodine in a reduced form as iodide is used for the determination of water by coulometric methods. The sample to be examined is introduced into the solution, and the iodide is then oxidized anodically to iodine.

Attempts have already been made to effect a partial replacement of the methanol used as the solvent in the one-component reagent by other solvents; in particular, benzene, dioxane, glacial acetic acid, ethanol, acetonitrile and dimethylformamide have been employed for this purpose (cf. Chemical Analysis, Volume 5, Aquametry, Part III, pages 101 and 102, 1980, 2nd edition, published by John Wiley & Sons).

Most of these substitutes had the disadvantage that they were not able to dissolve the amine salts formed, and they rendered the end point of the titration indistinct.

Further substitutes for methanol as a solvent in KF reagents are ethylene glycol monomethyl ether (2-methoxyethanol) (cf. Anal. Chem. 27 (1955), 450) and alkylene carbonates (cf. German Offenlegungsschrift 3,040,474 =U.S. Pat. No. 4,351,744).

The known solvents cannot be used without limitations. Methanol causes side reactions which interfere with, or even render impossible, the determination of water: aldehydes form acetals, various ketones form ketals, some carboxylic acids are esterified, silanols are etherified and certain amines are methylated. 2-Methoxyethanol exhibits a similar behavior, even though the activity is lower. Dimethylformamide affects the stoichiometry of the reaction and is not suitable for this reason. In principle, alkyl carbonates have the same disadvantage; in addition they dissolve the reaction products only to a very slight extent, so that the titration has to be carried out in a methanolic reaction medium, in which case side reactions again take place.

The object of the invention is to provide, for the determination of water, a solvent and a reagent which enable the analysis to be carried out in a substantially problem-free manner.

The invention relates to a solvent for the determination of water, which is composed of over 10% by weight of a monohydric or dihydric alkanol which has 1 to 3 carbon atoms and contains 1 to 4 halogen atoms and/or 1 to 4 optionally substituted phenyl radicals (the halogen atoms being attached to carbon atoms free from hydroxyl groups).

The invention also relates to a reagent for the determination of water, which contains sulfur dioxide, a base and iodine or an iodide as well as a solvent which is composed of over 10% by weight of a monohydric or dihydric alkanol which has 1 to 3 carbon atoms and which contains 1 to 4 halogen atoms and/or 1 to 4 optionally substituted phenyl radicals (the halogen atoms being attached to carbon atoms free from hydroxyl groups).

The invention also relates to a process for the determination of water in an organic solvent by the Karl Fischer method, which comprises using a monohydric or dihydric alkanol which has 1 to 3 carbon atoms and which contains 1 to 4 halogen atoms and/or 1 to 4 optionally substituted phenyl radicals (the halogen atoms being attached to carbon atoms free from hydroxyl groups) as the solvent or as a component of the solvent.

The essential characteristic of the invention is the use of specific aliphatic alcohols in the determination of water by the Karl Fischer method. In this case the alcohol acts as the sole solvent for the sample under investigation or is a constituent of the particular solvent used. The alcohol also acts as a solvent for the agents of the KF reagent or as a solvent component of the KF reagent. Certain monohydric or dihydric alkanols are suitable in accordance with the invention, namely alkanols which contain 1 to 3 carbon atoms and 1 to 4 halogen atoms and/or 1 to 4 phenyl radicals which can, in turn, carry substituents (the halogen atoms being attached to carbon atoms free from hydroxyl groups). The halogen atoms are bromine, iodine, fluorine, and preferably chlorine atoms, and the substituents located on the phenyl radicals are halogen atoms, lower alkyl radicals or lower alkoxy radicals containing in each case not more than 4 carbon atoms.

Examples of suitable alkanols are 2-chloroethanol, 2-bromoethanol, 2-iodoethanol, 2-fluoroethanol, 2,2,2-trichloroethanol, 2,2,2-tribromoethanol, 2,2,2-trifluoroethanol, 1-bromopropan-2-ol, 2-chloropropan-1-ol, 3-chloropropane-1,2-diol, 2,2,3,3-tetrafluoropropan-1-ol, benzyl alcohol, 2-bromobenzyl alcohol, 3-methoxybenzyl alcohol, 4-methoxybenzyl alcohol, 4-methylbenzyl alcohol, 1-phenylethanol, 2-phenylethanol, 2-phenoxyethanol, benzhydrol and tetraphenylethanediol. The alkanols are used individually or as a mixture with one another. If appropriate, they are employed as a mixture with another organic solvent, in which case the amount of the alkanol is more than 10, preferably at least 25, percent by weight of the mixture of solvents.

Suitable additional organic solvents are lower aliphatic alcohols, such as methanol, ethanol, propanol, ethylene glycol and ethylene glycol monomethyl ether and also, in particular, non-hygroscopic organic solvents which are free from hydroxyl groups, preferably liquid hydrocarbons and liquid halogenated hydrocarbons; the amount of this solvent in a given case is less than 90, preferably not more than 75, percent by weight of the mixture of solvents.

The additional solvent which is preferably employed is an aliphatic hydrocarbon having 5 to 10 carbon atoms, preferably 6, 7 or 8 carbon atoms, or an aromatic, optionally alkyl-substituted hydrocarbon having 6 to 12 carbon atoms, preferably 6, 7 or 8 carbon atoms. Examples of these are n-pentane, n-hexane, 2,3-dimethylbutane, 3-methylhexane, methylcyclopentane, n- heptane, cycloheptane, i-octane and decahydronaphthalene and also benzene, toluene, 1,2-diethylbenzene, xylene and 1,3-dimethylnaphthalene. The halogenated hydrocarbon is an aliphatic halogenated hydrocarbon having 1 to 10 carbon atoms, preferably 1 to 7 carbon atoms, or an aromatic halogenated hydrocarbon having 6 to 10 carbon atoms, preferably 6 or 7 carbon atoms. Examples of these are chloroform, methylene chloride, carbon tetrachloride, 1,1,2,2-tetrachloroethane, 1,1,1-trichloroethane, 2-bromobutane, 1-bromo-3-chloropropane, 1-chlorohexane, 1,2-dibromo-1,1-dichloroethane, 1,2-dibromo-1,1-difluoroethane, 1,2-dichloroethane, 1,6-dichlorohexane, 2,2-dichloropropane, 1-fluoroheptane, pentachloroethane and perfluorobutyl iodide and also chlorobenzene, 3-chlorotoluene, 4-bromochlorobenzene, 1,2-dibromobenzene, 1,4-difluorobenzene and 3-bromobenzotrifluoride.

The reagent according to the invention usually contains 0.1 to 10 moles, preferably 0.5 to 3 moles, of sulfur dioxide, 0.1 to 3 moles, preferably 0.1 to 1 mole, of iodine or an iodide and 0.1 to 10 moles, preferably 0.5 to 5 moles, of a base, in each case relative to 1 liter of reagent. The iodine-containing reagent is used for volumetric titration and the iodide-containing reagent is used for coulometric titration.

The sulfur dioxide is optionally employed as a mixture with an acid, preferably a carboxylic acid. The molar ratio of sulfur dioxide to acid is 20:1 to 1:5, preferably 2:1 to 1:2; the amount of sulfur dioxide is then reduced by the corresponding amount of acid. Examples of suitable acids are mineral acids, such as sulfuric acid and hydriodic acid, and also, in particular, carboxylic acids, such as benzoic acid and salicylic acid.

The base present in the reagent according to the invention is usually pyridine or 2-methylpyridine or an aliphatic amine which optionally contains 1,2 or 3 oxygen atoms, for example ethanolamine, diethanolamine and triethanolamine, or a five-membered or six-membered, optionally substituted heterocyclic compound containing at least 2 hetero-atoms, at least 1 hetero-atom being a nitrogen atom, for example imidazole and 2-methylimidazole. Salts of carboxylic acids, for example zinc acetate, sodium acetate and sodium benzoate, and also ammonium salts of carboxylic acids, for example ammonium acetate, ammonium benzoate, diethanolammonium acetate and diethanolammonium benzoate, are also suitable.

The reagent according to the invention is prepared by dissolving the agents in the particular solvent, which is at a temperature of 15° to 50° C., preferably 20° to 40° C.

The reagent is used for determining the water content of solid or liquid substances, and the determination is carried out volumetrically or coulometrically. The reagent can be employed either as a one-component reagent or as a two-component reagent. It is distinguished by the fact that the reaction which takes place in the water analysis is not interfered with. The end point of the titration is visually clearly recognizable.

The following examples serve to illustrate the invention in greater detail.

EXAMPLE 1

395 g (5 moles) of pyridine were dissolved in 500 ml of anhydrous benzyl alcohol at room temperature, and 96 g (1.5 moles) of sulfur dioxide were passed into the solution, with cooling, at a maximum temperature of 40° C. 80 g (0.31 mole) of iodine were then dissolved in the solution, and the whole solution was made up to 1 l with benzyl alcohol.

EXAMPLE 2

136 g (2 moles) of imidazole were dissolved in 600 ml of anhydrous 3-chloropropane-1,2-diol at room temperature, and 96 g (1.5 moles) of sulfur dioxide were passed into the solution, with cooling, up to a temperature of 40° C. 100 g (0.39 mole) of iodine were then dissolved in the solution, and the whole solution was made up to 1 l with 3-chloropropane-1,2-diol.

EXAMPLE 3

105 g (1 mole) of diethanolamine were dissolved in a mixture of 400 g of anhydrous 2-phenylethanol and 400 g of chloroform at room temperature, and 64 g (1 mole) of sulfur dioxide were passed into the solution, with cooling, up to a temperature of 30° C. The solution was then made up to 1 l with the solvent mixture mentioned (solution A).

30 g (0.12 mole) of iodine were dissolved in 500 ml of the solvent mixture mentioned (solution B).

EXAMPLE 4

82 g (1 mole) of 2-methylimidazole were dissolved in 1 l of anhydrous 2-chloropopan-1-ol at room temperature. 17 g (0.1 mole) of potassium iodide and 12.8 g (0.2 mole) of sulfur dioxide were then introduced into the solution, the temperature of the mixture being kept at 30° C. by cooling.

USE EXAMPLE 1

2 ml of acetic acid were dissolved in 50 ml of methanol and the mixture was titrated in a commercially available automatic titration apparatus with the reagent obtained in accordance with Example 1. The water content of the methanol was determined by an analogous titration.

USE EXAMPLE 2

25 ml of 3-chloropropane-1,2-diol were freed from water by titration with the reagent obtained in accordance with Example 2. 2 ml of acetone were weighed out into the dehydrated solvent, and the water content was determined by titration in a commercially available automatic titration apparatus.

USE EXAMPLE 3

30 ml of the solution A from Example 3 were freed from water by titration with the solution B belonging thereto. 2 ml of benzaldehyde were weighed out into the dehydrated solution and were titrated with solution B in a commercially available automatic titration apparatus.

USE EXAMPLE 4

Use Example 3 was repeated, but using a solution of 50 g (0.20 mole) of iodine in 1 l of xylene as the solution B.

USE EXAMPLE 5

50 ml of 2-chloroethanol were freed from water by titration with a commercially available KF reagent. (The reagent contained 0.35 mole of iodine, 1.5 moles of sulfur dioxide and 3.2 moles of pyridine per litre, as well as 2-methoxyethanol as the solvent.) 2 ml of methyl ethyl ketone were weighed out into the dehydrated solvent and were titrated with the abovementioned reagent.

USE EXAMPLE 6

25 ml of the reagent obtained in accordance with Example 4 were freed from water oxidatively in the anode compartment of a commercially available KF coulometer. 1 ml of formic acid was weighed out into the dehydrated solution and was titrated coulometrically.

I claim:

1. A reagent for the determination of water by the Karl Fischer Method, comprising sulfur dioxide, a base and iodine or an iodide and a solvent containing (a) more than 10 percent by weight of a monohydric or dihydric alkanol having 1 to 3 carbon atoms, which alkanol is substituted on its carbon atoms with 1 to 4 halogen atoms, 1 to 4 phenyl radicals or 1 to 4 substituted phenyl radicals, the halogen atoms being attached to carbon atoms free from a hydroxyl group, and (b) less than 90 percent by weight of an organic solvent selected from the group consisting of a lower aliphatic alcohol, a liquid hydrocarbon and a liquid halogenated hydrocarbon.

2. A reagent as recited in claim 1, wherein the amount of alkanol is at least 25 percent by weight and the amount of the organic solvent is not more than 75 percent by weight.

3. A reagent as recited in claim 1, wherein the alkanol contains chlorine atoms.

4. A reagent as recited in claim 1, wherein the liquid hydrocarbon is selected from the group consisting of an aliphatic hydrocarbon having 5 to 10 carbon atoms, an aromatic hydrocarbon having 6 to 12 carbon atoms, an aromatic hydrocarbon having 6 to 12 carbon atoms which is alkyl-substituted, a halogenated aliphatic hydrocarbon having 1 to 10 carbon atoms and a halogenated aromatic hydrocarbon having 6 to 10 carbon atoms.

* * * * *